(12) United States Patent
Wang et al.

(10) Patent No.: US 7,749,546 B2
(45) Date of Patent: Jul. 6, 2010

(54) COMPOSITION FOR EFFECTIVELY SUPPRESSING THE GROWTH OF PROSTATE CANCER CELL, SUPPRESSING THE PROSTATIC HYPERPLASIA AND ITS PREPARATION METHOD

(75) Inventors: Yu-Lung Wang, Danshuei Township, Taipei County (TW); Sheng-Yung Liu, Danshuei Township, Taipei County (TW); San-Bao Huang, Danshuei Township, Taipei County (TW)

(73) Assignee: Golden Biotechnology Corp., Taipei Country (TW)

( * ) Notice: Subject to any disclaimer, the term of this patent is extended or adjusted under 35 U.S.C. 154(b) by 0 days.

(21) Appl. No.: 11/293,314

(22) Filed: Dec. 5, 2005

(65) Prior Publication Data
US 2006/0134241 A1    Jun. 22, 2006

(30) Foreign Application Priority Data
Dec. 21, 2004    (TW) .............................. 93139733 A

(51) Int. Cl.
*A01N 65/00*    (2009.01)

(52) U.S. Cl. ...................................................... 424/725
(58) Field of Classification Search ....................... None
See application file for complete search history.

(56) References Cited

U.S. PATENT DOCUMENTS

| | | | |
|---|---|---|---|
| 6,455,078 B1 * | 9/2002 | Wu | 424/725 |
| 7,153,503 B1 * | 12/2006 | Henderson | 424/638 |
| 2005/0147699 A1 * | 7/2005 | Wu et al. | 424/757 |

OTHER PUBLICATIONS

Drugs.com, Astragalus, 6 pages, 2008.*
Immunulogy, 15 pages, 2005.*

* cited by examiner

*Primary Examiner*—Michael V Meller
(74) *Attorney, Agent, or Firm*—WPAT, P.C.; Anthony King

(57) ABSTRACT

A composition for effectively suppressing the growth of Prostate Cancer Cell, suppressing the Prostatic Hyperplasia and its preparation method, wherein this composition contains the *Astragalus* radix or its extracts with effective ingredients, which can either prevent or cure the Prostate cancer and suppress the Prostatic Hyperplasia as well.

1 Claim, 5 Drawing Sheets

Table 1

| Concentration ($\mu$g/mL) | Cell Survival Rate (%) | | | | |
|---|---|---|---|---|---|
| | Soy Isoflavones (Control group) | Astragalusradix extracts | PCF1-21 | PCF1-51 | PCF1-12 |
| 5.0 | 73±5 | 68±2 | 52±4 | 52±6 | 52±0 |
| 10 | 69±3 | 41±9 | 41±1 | 35±3 | 45±0 |
| 50 | 31±3 | 16±2 | 7.4±2.8 | 16±7 | 5.4±3.5 |
| IC$_{50}$ ($\mu$g/mL) | 30 | 8.4 | 6.1 | 5.6 | 6.2 |

Table 2

| PCF1 Concentration ($\mu$L/mL) | Cell Survival Rate (%) | |
|---|---|---|
| | PCF1 | Taxol+PCF1 |
| 0.0 | 100±9 | 56±6 |
| 0.1 | 99±3 | 43±0 |
| 1.0 | 58±6 | 31±2 |
| 10 | 18±5 | 14±7 |
| IC$_{50}$ ($\mu$L/mL) | 2.7 | 0.049 |

Table 3

| Group | | PSA(ng/mL) | Tumorweight(g) |
|---|---|---|---|
| Control | n=10 | 21.2±12.2 | 0.153±0.087 |
| PCF1, 0.3g/kg | n=10 | 9.1±8.0* | 0.078±0.063 |
| PCF1, 1g/kg | n=10 | 12.9±12.1 | 0.070±0.071* |
| PCF1, 3g/kg | n=9 | 14.9±14.6 | 0.093±0.083 |

Table 4

| | Cell Survival Rate (% of control) | |
|---|---|---|
| Concentration (μL/mL) | PCF1 liquid extractives | PCF1 alcohol extractives |
| 0.00 | 100 | 100 |
| 0.01 | 80.0 | 90.4 |
| 0.1 | 63.6 | 53.2 |
| 1 | 43.2 | 40.8 |
| 10 | 29.6 | 11.2 |
| IC501(μL/mL) | 0.019 | 0.033 |
| IC502(μL/mL) | 12.8 | 4.25 |

COMPOSITION FOR EFFECTIVELY SUPPRESSING THE GROWTH OF PROSTATE CANCER CELL, SUPPRESSING THE PROSTATIC HYPERPLASIA AND ITS PREPARATION METHOD

BACKGROUND OF THE INVENTION (a) Technical Field of the Invention

The present invention relates generally to a kind of composition for effectively suppressing the growth of Prostate Cancer Cell, suppressing the Prostatic Hyperplasia and its preparation method.

(b) Description of the Prior Art

The prostate cancer is a critical male cancer and even prostate cancer is the second leading cause of death among men in the western countries. In our country, the incidence rate of prostate cancer has been increasing year by year substantially.

According to the reports submitted by the National Cancer Institute of American, people who eat soybean products can reduce the incidence rate for prostate cancer. In light of the investigations, it shows that patient numbers relating to prostate cancer diseases in East Asia region is much less than Euro-American region, and the main reason disclosed might be involved in the possibility of daily digestible value of soybean (with effective composition of Soy Isoflavones) (Note 1), and many researches have disclosed that Soy Isoflavones is capable to reduce the incidence rate of prostate cancer (Note 2), in addition, the prostate cancer research projects held by the Harvard Medical School of American, had also confirmed that Soy Isoflavones can indeed suppress the growth of prostate cancer by the verification of animal experiments (Note 3).

Prostate, containing prostate cells (PZ-HPV-7 cells), which is a part of male reproductive system, locating at the urinary bladder-outlet and wrapping around the proximal urethra, most of male over 50 years old, almost have a Prostatism in a different level (due to human prostate cells (PZ-HPV-7 cells) containing the epidermal growth factor), which is a normal symptom, and thus results in the following effects:

1) Decreasing force of urination, it's difficult to start urine flow immediately.

2) Urinary frequency and noturia: Increasing urination times, getting up frequently to urinate at midnight.

3) Residual urine: still dribble a little urine after finished urinating.

4) Acute bladder hypotonicity: difficult to urinate suddenly while bladder is full.

5) Hematuria.

Other symptoms including:

Urinary tract infection: showing symptoms of frequent urination, having to pass urine suddenly or often, burning or pain while passing urine etc., and finding out pus cells and germs during cystourethroscopy inspection.

Bladder stone: causing pain during urination or sudden interruption of urinary stream.

Bladder Diverticulum: Bladder diverticula are herniations of the bladder mucosa through the bladder wall musculature, therefore it is necessary to have urination twice, due to the urine inside bladder is impossible to be passed out completely once, therefore needs to urinate the urine again from additional Diverticulums.

Urine overflow incontinence: overflow in bladder, and incontinence happened while pressure is exceeding the urethra resistance and pass urine out of control.

No matter the prostate cancer or the Prostatic Hyperplasia etc., it will cause a huge burden to national health insurance system in addition to the tremendous threat or perplexing to personal life quality, and thus it is the obligation for the medicine, pharmacy industry without any doubt to find out more effective drugs.

The applications of *Astragalus* radix had been recorded in various Traditional Chinese Medicine and Pharmacopoeia, according to <<Chinese Bencao>>(Shanghai Science and Technology Publishing House, 1999), based on the relevant researches in Mainland China during recent years, the *Astragalus* radix has various effects such as: to enhance the immunity function, improve the activity of killer cells, enhance the resistance to diseases, anti-aging, anti-oxidation and nutritional anemia treatment, improve the cardiovascular system, multiple virus resistance, and anti-cancers etc. Regarding the anti-cancers effect, it has been found out during animal experiments that the *Astragalus* radix is capable to reduce the occurrence rate of the big rats on lung cancers, to extend the lifetime of small rats suffered from melanoma, and there is at least one additional successful case for stomach cancer patient and two successful cases for ovarian cancer patients during clinical experiments, in which the cancer cells were killed by taking polysaccharides extract of Radix *Astragali*.

In light of the medical papers in the western countries, the *Astragalus* radix in vitro experiments shown that it has a effect in suppressing the stomach cancer cells (Note 4), and the result disclosed in the animal experiment, the *Astragalus* radix extracts are capable to effectively decrease the incidence rate of urinary bladder tumors caused by the carcinogen N-butyl-N'-the butanolnitrosoamine (Note 5), while taking together with other Chinese herbal medicines, it showed that the TCM Prescription containing Radix Angelicae Sinensis and Radix *Astragali* has suppressed cancer cells transformed underneath mice skins (Note 6), and the composition of Juzen-taiho-to which contains Cinnamate, Radix *Astragali* and another two kinds of Japanese herb medicines has a effect in suppressing the liver cells transformed by colorectal cancer cells as well as lung cells transformed by melanoma accordingly (Note 7), in addition, when TCM Prescription containing 10 different Chinese herb medicines including Radix *Astragali* to be used together with mitomycin C in order to treat mice having an implantation of blood cancer cells, it showed that the lifetime of these mice is longer than other mice having treatment of mitomycin C only (Note 8), in light of the above information, we found out that Radix *Astragali* has been utilized popularly in various experiments for cancer treatments, however until this moment, there is neither any research report related to the application of Radix *Astragali* on the treatment of prostate cancer nor any effects on suppressing Human's Prostatism as well.

Note 1—Yun, T. K. 1999. Ann. NYAcad. Sci., 889:157-92; Persky, V. and I. Van

Horn. 1995. J. Nutr., 125(3):709-712S; Messina, M., et. al., 1994. Nutr. Cancer, 21:113-131; Haytowitz, D. B. 1995 J. Nutr., 125:1952-1955

Note 2—Messina, M. J. 2003. Nutr. Rev., 61(4):117-31; Zhou, J. R. et. al.,

Prostate, 53:143-153.

Note 3—Prostate, 2002, 53:143-153.

Note 4—Linet. al., World J Gastroenterol. 2003.9:670.

Note 5—Kurashigeet. al., CancerInvest. 1999.17:30.

Note 6—Hsiehet. al., ImmunopharmacolImmunotoxicol. 2003.25:259.

Note 7—Onishiet. al., BiolPharmBull. 1998.21:761.

Note 8—Aburadaet. al., JPharmacobiodyn. 1983.6:1000

SUMMARY OF THE INVENTION

The primary purpose of the present invention is find out the effects for *Astragalus*radix extracts, which consists of four major ingredients, namely (1) Aminoacid (major ingredient of protein), (2) Polysaccharides (having a more tightening combination for Aminoacid), (3) Saponins (anti-inflammation), (4) Flavonoids (increasing estrogen to suppress androgen), and its compositions are capable to suppress the prostate cancer as well as suppress the Prostatic Hyperplasia, and in accordance with a series of experiments, in vitro, it has been verified that its effects is even much more effective than Soy Isoflavones. The present invention has verified that the *Astragalus*radix extracts, or a new composition of PCF1, which consists of effective extracted ingredients of *Astragalus*radix and Soy Isoflavones etc., and it shows that both effects of *Astragalus*radix extracts and new complex composition are capable to suppress both the growth of Prostate Cancer Cell and also the symptom of Prostatic Hyperplasia at the same time.

The foregoing object and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

Table 1 shows the growth-suppressing capability of PCF1 against the human prostate cancer LNCaP cell lines in different composition ratio;

Table 2 shows the growth-suppressing capability of Taxol against the human prostate cancer LNCaP cell lines with the assistance provided by PCF1;

Table 3 shows the suppressing capability of PCF1 against the blood levels of prostate specific antigen (PSA) and the growth of the prostate cancer tumor; and Table 4 shows the PCF1 is suppressing the growth of prostate cells PZ-HPV-7.

DETAILED DESCRIPTION OF THE PREFERRED EMBODIMENTS

The following descriptions are of exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

PRODUCTION EXAMPLE

Figure 1:
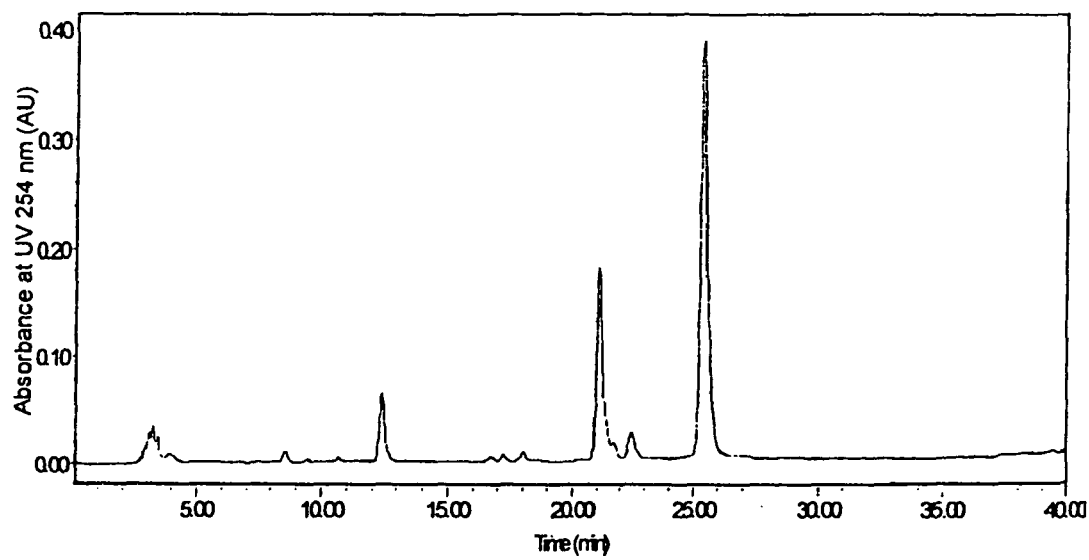
FIG. 1 is the high-performance liquid chromatographic profile of PCF1.
Figure 2:
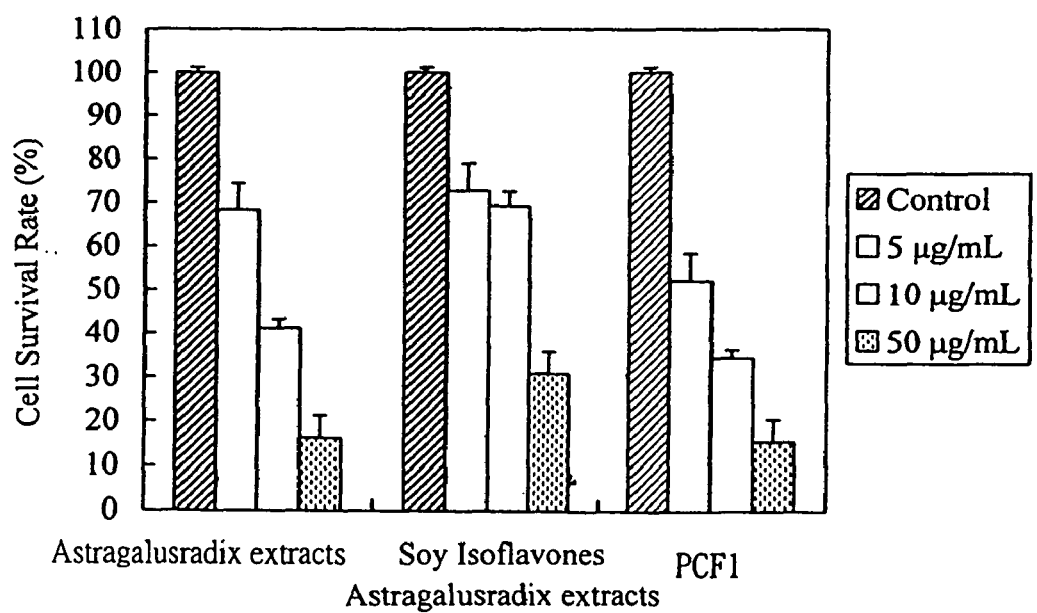
FIG. 2 is shows the comparable growth-suppressing capability against the human prostate cancer LNCaP cell lines among the Soy Isoflavones (control group), *Astragalus* radix extracts and PCF1.

The Production of *Astragalus* radix Extracts and Composition Containing *Astragalus* radix Extracts:

The *Astragalus* radix extracts, as cited by the general arts, can be made by grinding 100 g wild original *Astragalus* radix root material into small pieces, and then adding 2 L water, heating it until boiling point for recirculation about 1-4 hours, and then 30% *Astragalus* radix extract would be acquired by filtering, concentrating and drying the extractive solution; where the Soy Isoflavones containing 20% Aglycone Form which is bought from the market; and the new complex composition—PCF1, consisting of *Astragalus* radix extract and Soy Isoflavones having the specific gravity for extracts in a proportional ratio of 1:0 to 1:2, where its high-performance liquid chromatographic profile is shown in FIG. 1, and the high-performance liquid chromatographic instrument has a column of "ThermoHypersilKeystoneRPC18", 4.6. times. 0.250 mm; mobile phase for the high-performance liquid chromatographic instrument is 35% MeOH in 0minute, 70% MeOH in 30minutes, 35% MeOH in 35minutes, 35% MeOH in 40minutes, with content of 0.1% TFA; and the flow speed for the high-performance liquid chromatographic instrument is at 1 mL/min; where its detecting device is DAD, and wave length is set at 254 nm.

EXPERIMENTAL EXAMPLE I

In Vitro Mode Anti-tumor Activity Assay Example

Based on the anti-tumor drugs filter mode provided by the National Cancer Institute (NCI) in America, utilize in vitro filter mode for human prostate cancer cell lines—LNCaP cells. Where human prostate cancer cell lines—LNCaP cells is being cultured in the culture medium which is supplemented by fetalbovine serum for 24 hours, and then change the culture medium so as to culture it in a new culture medium by adding assay sample for 72 hours, afterwards evaluate the cell survival rate by MIT colorimetric analysis method.

EXPERIMENTAL EXAMPLE II

In Vitro Mode Adjunctive Treatment Activity Assay Example

Utilize in vitro filter mode for human prostate cancer cell lines—LNCaP cells. Where human prostate cancer cell lines—LNCaP cells is being cultured in the culture medium which is supplemented by fetalbovine serum for 24 hours, and process cells by Taxol for 72 hours, and then change the culture medium so as to culture it in a new culture medium by adding assay sample for 72 hours, afterwards evaluate the cell survival rate by MIT colorimetric analysis method.

※ The assay analysis of the compositions in accordance with the present invention in effect for suppressing the growth of human prostate cancer cells, wherein it is necessary to compute the cell survival rate for cells in each well of 96-well microplate, afterwards evaluate the cancer cells survival rate by MIT colorimetric analysis method.

※ MTT colorimetric analysis method: MTT is a kind of tetrazolium salt, with a full name of 3-[4,5-Dimenthylthialzol-2-yl]2, 5-diphenyltetrazoliumbromide, which is the yellow dye, capable to be absorbed by live cells and also be reduced to blue color formazan by succinate-tetrazoliumreductase in mitochondrion, which is commonly used for filtering the affection for matters to the growth and proliferation of cells.

EXPERIMENTAL EXAMPLE III

In Vitro Mode Immunomodulation Activity Assay Example

Utilize in vitro filter mode for human peripheral blood mononuclear cells (MNCs). Where MNCs is being cultured in the culture medium which is supplemented by fetalbovine serum also adding assay samples, such as TNF-α for 24 hours, or adding IFN-γ for 72 hours, and then analyze expression for both TNF-α and IFN-γ by means of TNF-α immunoassay kit and IFN-α immunoassay kit.

EXPERIMENTAL EXAMPLE IV

In Vivo Mode Anti-tumor Activity Assay Example

Utilize tumor animal mode for nude rats inoculated the human prostate cancer cell lines—LNCaP cells.

There are 6-weeks old male nude rats (BALB/c-nu/nu) used for the experimental animal mode. Where animals are cut open from abdomen after raised and trained, showing off the prostate, and then inoculating the human prostate cancer cell lines—LNCaP cells (2×106 cells/50µ LHBSS/rats) from back side of the prostate with a #30 needle, then use 5-0 threads to sew it up. After a regular feeding for 2 weeks, drawing up blood from each animal for measuring the serum PSA value, which are classified into 4 groups and each group would be processed as the following methods:

Control group: Freely taking the powder meal of rodent chow diet (Purina 5010) for 42 days.

PCF1 low-dose group (0.3 g/kgbw/day): Freely taking the powder meal of rodent chow diet (Purina5010) containing 0.3 g/kgbw/day for 42 days.

PCF1 medium-dose group (1 g/kgbw/day): Freely taking the powder meal of rodent chow diet (Purina5010) containing 1 g/kgbw/day for 42 days.

PCF1 high-dose group (3 g/kgbw/day): Freely taking the powder meal of rodent chow diet (Purina5010) containing 3 g/kgbw/day for 42 days.

EXPERIMENTAL EXAMPLE V

PCF1 in Vitro Mode Suppressing the Growth Activity of Human Prostate Cells Assay Example Utilize in vitro filter mode for human prostate cancer cell lines—LNCaP cells. Where human prostate cancer cell lines—LNCaP cells is being cultured in the Keratinocyte- Serum Free Medium which is supplemented by 5 ng/mLepidermal growth factor and bovine pituitary extract for 24 hours, and then change the culture medium so as to culture it in a new culture medium by adding assay sample for 48 hours, afterwards evaluate the cell survival rate by MIT colorimetric analysis method.

EMBODIMENT I

Figure 3:
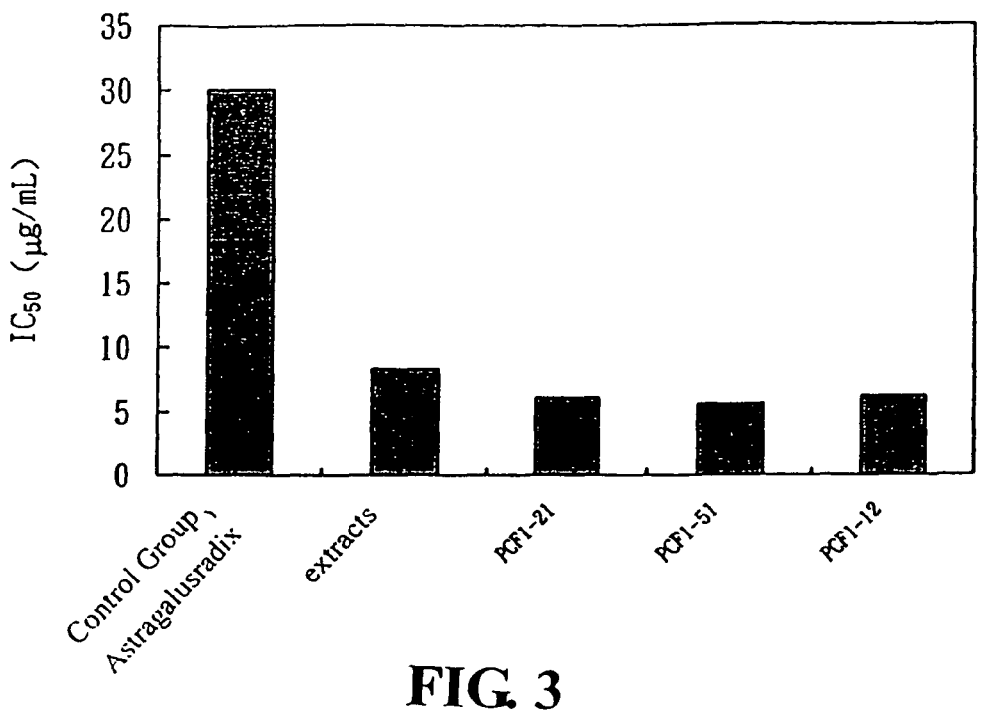
FIG. 3 shows the growth-suppressing capability of PCF1 against the human prostate cancer LNCaP cell lines in different composition ratio.

*Astragalus* radix Extracts Anti-tumor Activity:

According to the said method of in vitro mode anti-tumor activity assay example, where the concentration (IC50) required for the *Astragalus* radix extracts to suppress 50% growth rate of the human prostate cancer cells is 8.4 µg/mL, and the concentration (IC50) required for the Soy Isoflavones to suppress 50% growth rate of human prostate cancer cells is 30 µg/mL, where it is verified that the growth-suppressing effect for the *Astragalus* radix extracts on human prostate cancer cells is superior to the Soy Isoflavones respectively (as shown in Table 1 and FIG. 3).

EMBODIMENT II

PCF1-21 Anti-tumor Activity

According to the said method of in vitro mode anti-tumor activity assay example, while the proportional rate in-between the *Astragalus* radix extracts to Soy Isoflavones is 2:1, then it shows that the concentration (IC50) required to suppress 50% growth rate of the human prostate cancer cells is 6.1 µg/mL, meaning that the growth-suppressing effect for this composition on human prostate cancer cells is superior to either the *Astragalus* radix extracts or the Soy Isoflavones individually (as shown in Table 1 and FIG. 3).

EMBODIMENT III

PCF1-51 Anti-tumor Activity

According to the said method of in vitro mode anti-tumor activity assay example, while the proportional rate in-between the *Astragalus* radix extracts to Soy Isoflavones is 5:1, then it shows that the concentration (IC50) required to suppress 50% growth rate of the human prostate cancer cells is 5.6 µg/mL, meaning that the growth-suppressing effect for this composition on human prostate cancer cells is superior to either the *Astragalus* radix extracts or the Soy Isoflavones individually (as shown in Table 1 and FIG. 3).

EMBODIMENT IV

PCF1-12 Anti-tumor Activity

According to the said method of in vitro mode anti-tumor activity assay example, while the proportional rate in-between the *Astragalus* radix extracts to Soy Isoflavones is 1:2, then it shows that the concentration (IC50) required to suppress 50% growth rate of the human prostate cancer cells is 6.2 µg/mL, meaning that the growth-suppressing effect for this composition on human prostate cancer cells is superior to either the *Astragalus* radix extracts or the Soy Isoflavones individually (as shown in Table 1 and FIG. 3).

EMBODIMENT V

PCF1 Adjunctive Treatment Activity

According to said method of in vitro mode adjunctive treatment activity assay example, where the 2nMTaxols and 1 μL/mLPCF 1 activating individually, which achieves the cell survival rate of 56.4% and 57.6% for human prostate cancer cells respectively, while it is pre-processed (or post-processed) in conjunction with Taxol and PCF1 respectively, which achieves the cell survival rate of 30.8% for human prostate cancer cells respectively, meaning that PCF1 is capable to assist the Taxol in suppressing the growth of human prostate cancer cells (as shown in Table 2).

EMBODIMENT VI

PCF1 Immunomodulation Activity

Figure 4:
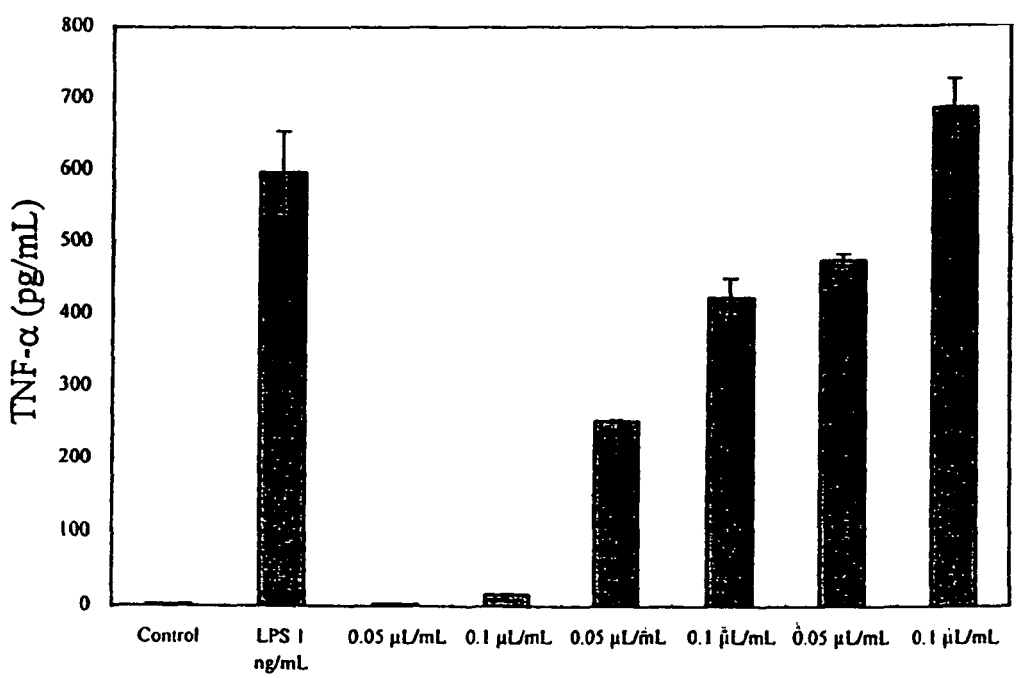
FIG. 4 shows the capability of human $_{Leukocyte}$ cells to release TNF-α which is activated by PCF1.
Figure 5:
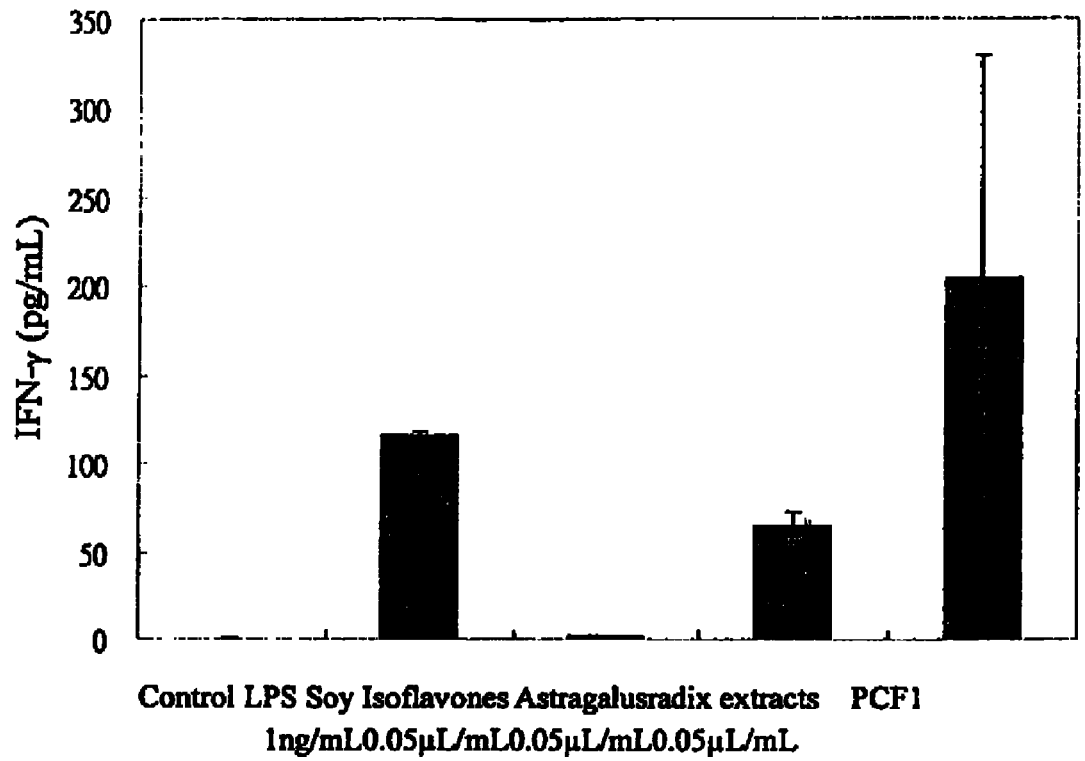
FIG. 5 shows the capability of human $_{Leukocyte}$ cells to release IFN-γ which is activated by PCF1.

According to said method of in vitro mode immunomodulation activity assay example, where the *Astragalus* radix has a function for activating the human leukocyte cell to release the TNF-.alpha. and IFN-.gamma., but the Soy Isoflavones has not, and the result showing that PCF1 is capable to activate the human leukocyte cell to release the TNF-.alpha. and IFN-.gamma. which is even superior to the *Astragalus* radix (as shown in FIG. 4, FIG. 5).

EMBODIMENT VII

PCF1 Anti-tumor Activity

According to said method of In vivo mode anti-tumor activity assay example, after feeding the animals with PCF1 low-dose (0.3 g/kgbw/day) continuously for 42 days, its blood PSA value is 9.1 ng/mL which is obviously much lower than that of control group, which is 21.2 ng/mL, where the suppressing rate reaches 57%, and the effective growth-suppressing rate for tumor achieves 49% (as shown in Table 3).

EMBODIMENT VIII

PCF1 Suppressing the Prostatic Hyperplasia Activity

Figure 6:
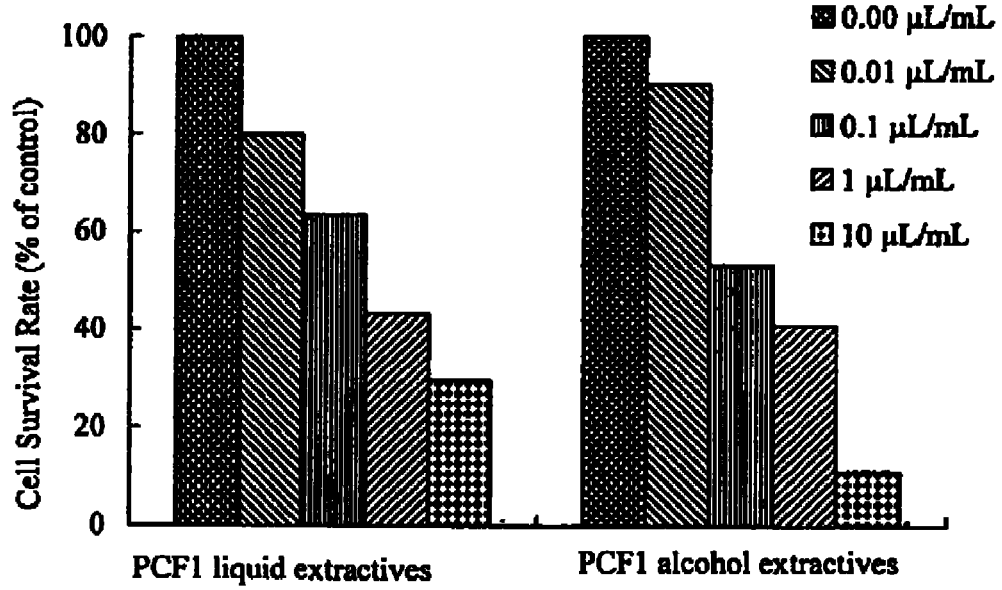
FIG. 6 shows the PCF1 is suppressing the growth of prostate cells PZ-HPV-7.

According to said method of in vitro mode activity assay example, it shows that concentration (IC50) required for the extractive solution of PCF1 and alcohol to suppress 50% growth rate of the human prostate cancer cells is 0.019 μL/mL and 0.033 μL/mL respectively, meaning that PCF1 is effectively suppressing the growth of human prostate cells (as shown in Table 4 and FIG. 6).

While analyzing the different proportional ratio for each composition in accordance with the present invention resulting in effects in suppressing the growth of cancer cells, we have realized the fact while the proportional weight rate in-between the *Astragalus* radix to the Soy Isoflavones is in the combination of 1:2-5:1, the composition will have a effective effect in growth-suppressing the human prostate cancer cells obviously, and among them the most superior proportional rate for the said composition is 5:1, as shown in FIG. 3, in addition, it has been verified by the animal experiments that the composition of the present invention is capable to effectively suppress the increasing of the blood PSA value as well as the growth of tumors consequently.

The present invention has successfully found out the medicine with *Astragalus* radix or its composition having an excellent effect in growth-suppressing the prostate cancer cells, where its effects of anti-cancer and cancer prevention have been verified in various theses or reports already, which is much superior to the Soy Isoflavones, and more over, the composition according to the present invention also has an effect in adjunctive treatments which is applicable to assist the anti-cancer drugs such as Taxol in suppressing the growth of prostate cancer cells, and meanwhile it has am additional function of the immunomodulation as well, which is capable of activating the leukocyte cells to release both the TNF-α and IFN-γ accordingly.

In light of the above description, due to the present invention has all the said advantages as well as practical values, where there is no any similar product which has ever been disclosed at all, thus the inventor believes that the present invention shall meet all the requirements for the application of the patent of new invention accordingly.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

What is claimed is:

1. A composition consisting of *Astragalus* radix extract and Soy Isoflavones having a ratio of 1:2, 2:1 or 5:1, respectively.

* * * * *